United States Patent [19]

Cosyns et al.

[11] 3,992,468

[45] Nov. 16, 1976

[54] PROCESS FOR THE CATALYTIC HYDRODEALKYLATION OF ALKYLAROMATIC HYDROCARBONS

[75] Inventors: Jean Cosyns, Nanterre; Bernard Juguin; Jean-Francois Le Page, both of Rueil Malmaison; Jean Miquel, Paris, all of France

[73] Assignee: Institut Francais du Petrole, Rueil-Malmaison, France

[22] Filed: Feb. 24, 1975

[21] Appl. No.: 552,278

[30] Foreign Application Priority Data

Mar. 1, 1974   France .............................. 74.07340
Apr. 29, 1974   France .............................. 74.15166
Sept. 9, 1974   France .............................. 74.30692

[52] U.S. Cl. ............................................ 260/672 R
[51] Int. Cl.² ........................................... C07C 3/58
[58] Field of Search ..................................... 260/672

[56] References Cited
UNITED STATES PATENTS

| | | | |
|---|---|---|---|
| 2,422,673 | 6/1947 | Haensel et al. ................. | 260/672 R |
| 3,530,194 | 9/1970 | Quik et al. ...................... | 260/672 R |
| 3,679,768 | 7/1972 | Kmecak et al. ................. | 260/672 R |
| 3,700,745 | 10/1972 | Kovach et al. .................. | 260/672 R |
| 3,760,023 | 9/1973 | Patrick et al. ................... | 260/672 R |

*Primary Examiner*—C. Davis
*Attorney, Agent, or Firm*—Millen, Raptes & White

[57] ABSTRACT

Process for hydrodealkylating alkylaromatic hydrocarbons using a catalyst comprising at least two metals deposited on a carrier, a first of these two metals being selected either from the group consisting of cobalt, ruthenium, osmium, palladium, rhodium, iridium and platinum or from the group consisting of chromium, molybdenum, tungsten and manganese, and the second of these two metals being selected from zinc, cadmium, gallium, indium, thallium, manganese, copper, silver, gold, yttrium, titanium, niobium, tantalum, chromium, molybdenum, tungsten, rhenium, germanium, tin and lead.

26 Claims, No Drawings

PROCESS FOR THE CATALYTIC HYDRODEALKYLATION OF ALKYLAROMATIC HYDROCARBONS

This invention concerns a new process for catalytically hydrodealkylating alkyl aromatic hydrocarbons to benzene. The alkyl aromatic hydrocarbons are either toluene or various xylenes or any alkyl aromatic hydrocarbon having nine or more carbon atoms in the molecule or an alkyl naphthalene hydrocarbon etc.

The feed charge subjected to hydrodealkylation contains one of the above-mentioned hydrocarbons in a pure state or a mixture of said hydrocarbons, in the presence or the absence of various hydrocarbons, for example in the presence of paraffins. The cuts containing aromatic hydrocarbons subjected to hydrodealkylation are generally produced from various sources such as the effluents from reforming units or from units performing various pyrolysis processes, for example, steam-cracking. The aromatic cuts which are used as feed charge for the hydrodealkylation process and which are produced from the above-mentioned sources may also have been subjected to various purification treatments by distillation and extraction as well as to treatments for increasing their total content of aromatic hydrocarbons and for simultaneously decreasing their naphthene and paraffin content. These various treatments (which are sometimes called aromatizing) have been described in detail, for example, in the French patent of addition No. 2,170,899 and in the French patent application No. 73/00806. The cuts subjected to hydrodealkylation may also have been subjected to treatments for removing certain constituents such as sulfur, nitrogen, various metals, etc.

According to the prior art, it was necessary, in practice, to proceed under very drastic conditions of temperature and pressure as well as at very low spatial velocities which made use of such processes very difficult and costly. Thus, for example, in the thermal processes, it is often necessary, in order to obtain significant yields, to operate at temperatures of at least 700° C, under pressures of at least 40 kg/cm$^2$, and at spatial velocities of at most 1. The catalytic processes generally make use of catalysts based, for example on chromium or molybdenum oxide, and are operated under similar conditions of pressure and spatial velocities and at temperatures not substantially lower than 700° C.

Another inconvenience of these processes is the formation of by-products consisting of very heavy aromatic hydrocarbon precursors of coke, which clog the catalyst and the reactor and which are detrimental to the yield of the operation. The process of the invention may optionally be performed under very favorable operating conditions; as a matter of fact, it can be operated under the following conditions: temperature from 400° to 650° C and, preferably, from 500° to 620° C, pressure from 1 to 40 kg/cm$^2$, more particularly from 1 to 30 and preferably from 1 to 20 kg/cm$^2$, spatial velocities from 1 to 10 and preferably from 2 to 8. The ratio of the hydrogen to the hydrocarbon, expressed in mole per mole, at the outlet of the reactor, is from 1 to 10 and preferably from 3 to 8. The process according to the invention may be performed under favorable operating conditions whereby good yields are achieved and consists of contacting the alkyl aromatic feed charge, under the above-mentioned conditions, with hydrogen in a reaction zone in the presence of either of a catalyst A or a catalyst B defined as below:

The catalyst A essentially contains:
a. a carrier
b. at least one metal selected from the group consisting of the metals from group VIII of the periodic classification of elements and,
c. at least one metal selected from the group consisting of zinc, cadmium, gallium, indium, thallium, copper, silver, gold, yttrium, titanium, niobium, tantalum and manganese.

The metals from group VIII are selected from cobalt and the noble metals from group VIII, i.e. ruthenium, osmium, palladium, rhodium, iridium and platinum.

For sake of stability, it may be advantageous, in some cases, to make use of couples of metals from group VIII such as the following couples: platinum-iridium, platinum-ruthenium or iridium-ruthenium etc.

The content by weight of the catalyst in noble metal from group VIII (or from each of the noble metals from group VIII when the catalyst contains several metals from this group) will be from about 0.05 to 5%, preferably from 0.1 to 1%. When the catalyst contains couples of noble metals from group VIII, the atomic ratio between the two metals of the couple may be, for example, from 0.1 to 20.

By way of example, in a catalyst having a total metal content of 1%, the content of one of said metals may be from 0.1 to 0.9% while the content of the other metal will be the complementary amount.

When using cobalt as metal from group VIII, the cobalt concentration will be from 0.05 to 20 % and preferably from 1 to 17% by weight of the catalyst.

The content by weight of the catalyst of metal selected from the group consisting of zinc, cadmium, gallium, indium, thallium, manganese, copper, silver, gold, yttrium, titanium, niobium and tantalum, is generally from 0.05 to 5% and preferably from 0.1 to 2%.

When the catalyst contains couples of the latter metals, the atomic ratio between the two metals of the couple may be, for example, from 0.1 to 20.

The catalyst B essentially contains:
a. a carrier,
b. at least one metal selected from a first group consisting of chromium, molybdenum, tungsten, rhenium and manganese, the metal concentration being from 0.05 to 20% by weight with respect to the catalyst and preferably from 0.1 to 10%. When catalyst B contains couples of metals from the first group, the atomic ratio between the two metals of the couple may be, for example, from 0.1 to 20.

By way of example, for a catalyst having a total metal content of 10%, the content of one of the metals from the first group, may be from 0.1 to 9.9% while the content of the other metal will be the complementary amount.

c. at least one additional metal, said additional metal being chosen different from the selected metal of the first group, this additional metal being selected from chromium, molybdenum, tungsten, rhenium, manganese, copper, silver, gold, zinc, cadmium, gallium, indium, thallium, germanium, tin and lead, the metal concentration being from 0.05 to 20% by weight of the catalyst and preferably from 0.1 to 5%. When the catalyst contains couples of the latter so-called additional metals, the atomic ratio between the two metals of the couple may be, for example, from 0.1 to 20.

All the above-mentioned metals which are constituents of catalysts A and B are deposited on a carrier selected among known carriers, for example, alumina, magnesia, magnesia-silica, acidic alumina, chlorinated and/or fluorinated alumina, for example alumina-silica, zirconia and zirconia-silica, the molecular sieves or zeolites and so on. It may be advantageous to make use of a carrier whose physical characteristics are such as to obtain a final catalyst having a specific surface from 1 to 100 m$^2$/g, preferably from 5 to 80 m$^2$/g, more particularly from 5 to 55 m$^2$/g and specially from 10 to 55 m$^2$/g the total pore volume of such a catalyst is preferably from 0.2 to 0.8 cc/g, preferably from 0.3 to 0.7 cc/g, 75% at least of the corresponding pores having an average diameter from 100 to 150 angstroms; the heat of neutralization of the catalyst by ammonia adsorption is then preferably lower than 10 calories and, more particularly, lower than 7 calories per gram of catalyst at 320° C under a pressure of 300 mm Hg. Accordingly, it is apparent that the acidity of the carrier is low.

The acidity of the catalyst may be determined by a known test of ammonia adsorption of the type described, for example, in "Journal of Catalysis, 2, 211–222 (1963)": the method consists of heating the catalyst at 600° C under vacuum (under a pressure lower than about 0.1 mm Hg) up to a complete gas removal (to remove water and undesirable impurities); then the catalyst is placed in a calorimeter at 320° C; ammonia is introduced in such an amount as to obtain a final pressure of the system at equilibrium of 300 mm Hg and the amount of heat evolved is measured. It must be noted that the heat of neutralization of the carrier forming part of the hydrodealkylation catalyst is substantially identical to that of the catalyst itself and that, also, the specific surface and the pore volume of the carrier are substantially identical to the above-mentioned values given for the catalyst itself.

When alumina of low acidity is used as the carrier, this alumina is characterized not only by its neutralization heat but also by its inertness to cracking and coking reactions in the presence of hydrogen. This determination may be carried out in any convenient manner. By way of example, it is possible to make use of the test of cracking of an easily crackable molecule such as n-heptane which may be cracked at temperatures substantially lower than the temperature required for cracking alkyl aromatic hydrocarbons. The alumina may be considered as inert when, at 500° C, the n-heptane injected at a spatial velocity of 1 on a carrier arranged in fixed bed in a reactor, under a hydrogen pressure of 20 bars and at a flow rate of the latter of 4 moles per mole of n-heptane of the charge, is recovered at the outlet of the reactor in a proportion of at least 99% by weight with respect to the introduced amount.

As alumina which can be used as carrier, the gamma alumina balls are particularly convenient. It is also possible to use other alumina conglomerates such as extrudates or pills.

The method of manufacturing the catalyst is not a critical feature of the invention, and any known method may be used. The active elements may, for example, be deposited separately, or preferably simultaneously on the carrier by impregnation of the latter by solutions containing the same, for example, aqueous solutions (or solutions in a suitable solvent) of halides, nitrates, acetates, oxalates of the above-mentioned elements; particularly aqueous solutions of cobalt nitrate, platinum chloride, iridium chloride, rhodium chloride, ruthenium chloride, hexachloroplatinic acid and hexachloroiridic acid. Also usable are chromates, molybdates, tungstates, rhenates and the chromic anhydrides, chloroplatinic acid, chloroiridic acid and their ammonium and amine salts, complexes containing said elements, for example, those formed with oxalic acid and the oxalates, with citric acid and the citrates, with tartric acid and the tartrates, with other polyacids and acid alcohols or their salts, the acetyl acetonates etc. and any other inorganic or organo-metallic derivative of elements such as chromium, molybdenum, tungsten, rhenium, cobalt, rhodium, ruthenium, palladium, iridium, platinum and osmium. For the introduction of the other cited metals, use simple or complex salts and the organo-metallic derivatives and other derivative salts or compounds of copper, silver, gold, yttrium, cerium, titanium, niobium, tantalum, zinc, cadmium, gallium, indium, thallium, manganese, germanium, tin and lead. We can further mention the noble hexachlorometallates of galium etc. are used. This list is not limitative and any other organo-metallic salt compound soluble in water or in organic solvents may also be used.

It is possible, in order to optimize and provide for the association of two, three or more elements constituting the active phase of the catalyst, to use derivatives, complex or simple, containing the active elements in the same molecule.

After the metal elements, are deposited on a carrier, the catalyst is then dried, roasted by heating under an oxidizing, reducing or inert atmosphere, according to the case, at a temperature from, for example, 300° to 600° C and then reduced in a hydrogen stream at a temperature, for example, from 350° to 700° C for 2 to 30 hours at a hydrogen flow rate of from 100 to 1,000 times the catalyst volume. The latter operation is preferably conducted in the hydrodealkylation reactor. It is also possible to omit the roasting step and to proceed directly to the reduction step.

For performing the reduction, it is not strictly necessary to make use of hydrogen since other reducing agents can be used, such as: hydrazine, carbon monoxide, alkyl metals (aluminum, zinc, etc.). The reduction can be performed as well in a gaseous medium as in a liquid medium.

The hydrodealkylation treatment may be conducted in at least one reaction zone, i.e. in at least one reactor, by making use of:

1. Either one or more fixed bed reactors, with the optional provision of an additional reactor which is operated when the catalyst is regenerated in one of the fixed bed reactors;

2. or one or more fluid bed reactors;

3. or, and this is often one of the best solutions when it is desired to proceed in a continuous manner over long periods, at least one moving bed reactor; the method (described in the French patent specification No. 2,160,269), consisting of circulating the charge and hydrogen through at least one reaction zone containing a catalyst, for example, in a granular form, the catalyst being progressively introduced at one end of the reaction zone and progressively withdrawn from the other end of said reaction zone, and then of conveying the catalyst progressively withdrawn from the reaction zone to a regeneration zone from where the catalyst, after regeneration and reduction in the presence of a hydrogen stream, is progressively reintroduced at the end of the reaction zone opposite to that from which the catalyst had been withdrawn, in order to replace the withdrawn catalyst in the reaction zone, thereby maintaining a high level of activity which is substantially constant at each point of the reaction zone.

The catalyst is withdrawn from the moving bed reactor or from each moving bed reactor in case of several reactors, in a progressive manner as above stated, which means that the catalyst may be withdrawn:

either periodically, for example at a rate of one tenth every 10 days, each withdrawal being limited to only a fraction of, for example, from 0.5 to 15% of the total amount of the catalyst. However, it is also possible to withdraw this catalyst at a much more rapid rate (for example of the order of 1 minute or 1 second), the withdrawn amount being proportionally reduced;

or in a continuous manner.

The moving bed reactor or reactors, in the case of several reactors, as well as the regeneration zone, may be placed at will, for example side by side. It may thus be necessary to repeatedly convey the catalyst from a relatively low point to a relatively high point, for example from the bottom of the reaction zone to the top of the regeneration zone; this conveyance may be achieved by means of any suitable device, such for example as a "lift". The fluid of the lift used for conveying the catalyst may be any convenient gas, for example nitrogen or still hydrogen, more particularly purified hydrogen.

The solid which is thus displaced through the one or more moving bed reactors may be a granular catalyst containing a convenient carrier: this catalyst may be, for example, in the form of spherical balls, having a diameter generally from 1 to 3 mm, preferably from 1.5 to 2 mm, these values being however not limitative. The bulk density of the catalyst may be for example, from 0.4 to 1, preferably from 0.5 to 0.9, and more particularly from 0.6 to 0.8, these values being not limitative.

The regeneration of the catalyst is achieved by any known means or still according to the method described for example in the French patent No. 2,160,269.

When using an alumina which is deemed of a too high acidity (e.g. when a metal is introduced by means of a solution of a compound containing halogen, it remains or it may remain small halogen amounts even after the final roasting of the catalyst, which may be detrimental to the performance of the catalyst, and which are therefore preferably removed), this acidity may be modified by adding, before or after the introduction of the active elements, certain compounds capable to modify either by themselves or by the effect of the products formed therewith after their decomposition on the carrier, under suitable conditions, the surface acidity of the solid.

According to the case, there can be used derivatives of metals from groups I A, II A (i.e. alkali or alkaline-earth metals) or still elements which, by their nature, are capable to modify the acidity of the carrier while simultaneously introducing some or even all the properties which must be imparted to the final catalyst (activity, selectivity, life time, resistance to poisoning, etc.)

Said metal derivatives or, more generally, active elements, need not to be introduced in an amount of more than 5% or even 2% by weight with respect to the final catalyst.

The following examples, which are not limitative, illustrate the invention.

EXAMPLE 1

We make use of a catalyst No 1 having an alumina carrier whose characteristics are as follows:
specific surface: 9.5 m$^2$/g
pore volume: 0.48 cc/g
percent of n.heptane cracked in the conditions hereinbefore described in the general statement: 0.8% by weight
neutralization heat (NH3): 3.5 cal/g$^2$ under the above-mentioned conditions.

Catalyst No 1 is prepared by dry impregnation of 100 g of alumina with 60 cc of an aqueous solution containing 2.30 g of manganese nitrate. Homogeneization occurs in one hour. The solid is dried at 110° C and roasted at 500° C with an air stream at a rate of 20 liters per liter of catalyst and per hour.

The resulting solid is then impregnated with 100 cc of an aqueous solution containing 16.7 g of a chloroiridic solution, containing 2.4% by weight of iridium. The contact is performed over 2 hours while stirring intermittently. The next steps are centrifugation, drying and roasting as above.

The finished catalyst contains 0.4% by weight of iridium and 0.5% of manganese. Its specific surface is 9 m$^2$/g, its pore volume: 0.45 cc/g and its heat of neutralization by ammonia adsorption is 3 calories per gram of catalyst at 320° C under a reduced pressure of 300 mm Hg.

The catalyst is then charged into a tubular reactor and reduced in a hydrogen stream at 550° C for 15 hours.

Over this catalyst, we pass a charge under the following operating conditions:
total pressure: 12 kg/cm$^2$
temperature: 550° C
VVH: 4 volumes of liquid charge per volume of catalyst and per hour,
hydrogen relative flow rate: 5.7 moles per mole of hydrocarbon of the feed charge.

The compositions of the charge and of the reactor effluent after cooling and separation of the hydrogen from the hydrocarbon gases are summarized in table I below:

TABLE I

| COMPOSITION BY MOLE % | CHARGE | EFFLUENT |
|---|---|---|
| n.hexane | 0.5 | — |
| benzene | 4 | 54.2 |
| toluene | 70 | 41.0 |
| ethyl benzene | 17 | 2.3 |
| xylenes | 8.5 | 2.3 |
| heavy products (aromatic having more than 8 carbon atoms) | — | undetectable |

Furthermore, it is observed that substantially no degradation of the aromatic ring occurs, the total number of aromatic moles which is recovered corresponding, except for a difference due to the experimental errors, to the total number of moles introduced into the reactor. The gaseous hydrocarbons, result substantially exclusively from the dealkylation of alkyl aromatic hydrocarbons or from the cracking of paraffins already present in the feed charge. The benzene yield obtained is, accordingly, determined easily from the data of Table I. In the present case it is 54.4 moles of benzene produced per each 100 moles of aromatics charged into the reactor. It must be noted also that this yield is maintained remarkably stable over the entire test period of 300 hours.

It is also remarkable that the formation of heavy products is not detectable and that the coke content of the catalyst after this test was found nill.

EXAMPLE 1 A (comparative)

In this example, we compare the performances obtained with the catalyst described in example 1 and those obtained with a catalyst No 2 containing 0.4% of iridium and 0% of manganese.

This catalyst and that of the invention have been tested under the same conditions as in example 1.

The benzene yields as well as the percent of formed heavy products with respect to the feed charge are compared in table II.

TABLE II

| REACTION TEMPERATURE °C | CATALYST No 1 ACCORDING TO THE INVENTION YIELD % BY MOLE (Ex.1) | | CATALYST No 2 OF EXAMPLE 1 A YIELD % BY MOLE | |
|---|---|---|---|---|
| | BENZENE | $C_9^+$ PRODUCTS | BENZENE | $C_9^+$ |
| 550 | 54.2 | — | 51 | 0 |
| 570 | 71 | 0 | 66 | 0 |
| 590 | 85 | 0 | 78 | <0.1 |
| 600 | 86 | 0.1 | 78 | 0.1 |

It is apparent that the catalyst of the invention provides a benzene yield substantially higher than that obtained with the other catalyst.

The introduction of manganese gives to the catalyst a better activity and selectivity.

EXAMPLE 1 B (comparative)

By way of comparison, the feed charge of example 1 is hydrodealkylated in the presence of a conventional hydrodealkylation catalyst No 3, containing 7.5% of chromium oxide deposited on alumina having a specific surface of 170 m²/g, a pore volume of 0.60 cc/g and a heat of neutralization by ammonia adsorption of 18 calories per gram of catalyst at 320° C under a reduced pressure of 300 mm Hg.

When operating under the same conditions as in example 1 (550° C, 12 kg/cm², VVH : 4 and with a hydrogen relative flow rate of 5.7 moles per mole of hydrocarbon of the feed charge), we obtain, after 300 hours, a benzene yield of 4% by moles and a molar percentage of $C_9^+$ of 0%.

These results are very poor.

When operating now in a conventional manner at 650° C, under a pressure of 40 kg/cm² with a VVH of 1 and a ratio $H_2/H_C$ of 5, we obtain, after 300 hours, a benzene yield of 58% by mole with a $C_9^+$ mole percent of 3.5%.

These results are acceptable but however, substantially less than those achieved by operating according to the invention, i.e. with a catalyst such as described in example 1 and under milder conditions. When in these two experiments with a chromium catalyst, we replace the alumina (having a specific surface of 170 m²/g) by that used in example 1, we obtain substantially the same results as in these two experiments.

EXAMPLE 1 C (comparative)

By way of comparison, we make use of catalysts No 1 and 2 of examples 1 and 1 A for hydrodealkylating the feed charge of example 1 under the following conventional operating conditions:
temperature: 650° C
pressure: 40 kg/cm²
VVH: 4
ratio $H_2/H_C$: 5

After 300 hours, we obtain, with the catalyst of example 1 above, a benzene yield of 84.5% by mole and a $C_9^+$ molar proportion of about 2% as compared with a benzene yield of 75% and a $C_9^+$ molar proportion of 0.3% for the iridium-containing catalyst of example 1 A. Proceeding at a too high temperature has the disadvantage of leading to the formation of heavy products which, on the contrary, are not formed when proceeding under milder conditions.

EXAMPLE 2

This example relates to a series of catalysts having as carrier the same alumina as that used in example 1.

A list of these catalysts as well as their composition by weight is given below:

| Catalysts | | |
|---|---|---|
| No 4 | 0.4 % platinum | 0.5 % manganese |
| No 5 | 0.4 % platinum | 0.5 % cadmium |
| No 6 | 0.4 % platinum | 0.5 % gallium |
| No 7 | 0.4 % platinum | 0.5 % indium |
| No 8 | 0.4 % platinum | 0.5 % thallium |
| No 9 | 0.4 % platinum | 0.5 % zinc |

These catalysts are obtained by double impregnation of the carrier according to the technique already described in example 1, although this technique is not the only one which can be used.

As a matter of fact, these catalysts give results which are of the same order of magnitude when prepared with a single impregnation. i.e. with a solution containing both associated elements, as when prepared by double impregnation, comprising first introducing the platinum element, then drying and roasting and thereafter introducing the second element.

These various catalysts are then charged into a tubular reactor, reduced at 550° C for 15 hours under a hydrogen stream, tested in the conditions of example 1 with the feed charge described in example 1. The benzene yields obtained after 100 hours of run, on these various catalysts are summaryzed in table III.

TABLE III

| CATALYST | 4 | 5 | 6 | 7 | 8 | 9 |
|---|---|---|---|---|---|---|
| BENZENE YIELD MOLE % | 54.3 | 54 | 54 | 54 | 55 | 54 |

EXAMPLE 3

In this example, we prepare a series of bimetallic catalysts with the same alumina carrier as in example 1.

The list of these catalysts as well as their compositions by weight is given below:

| | |
|---|---|
| catalyst 10 : 0.4 % iridium | 0.5 % zinc |
| catalyst 11 : 0.4 % ruthenium | 0.5 % manganese |
| catalyst 12 : 0.4 % rhodium | 0.5 % gallium |
| catalyst 13 : 0.4 % palladium | 0.5 % cadmium |
| catalyst 14 : 0.4 % cobalt | 0.5 % manganese |

The catalysts are obtained by impregnating the alumina carrier with an aqueous solution containing, on the one hand, salts of iridium, ruthenium, rhodium, palladium and cobalt, such as hereabove described and on the other hand, zinc, manganese, gallium and cadmium chlorides. The resulting solids, after impregnation, are then treated in the same manner as the catalysts of example 1, with the exception of the reduction step which is conducted at 580° C for 15 hours.

The results obtained after the test, conducted in the same conditions as those of example 3, are summarized in table IV below:

TABLE IV

| CATALYST | 10 | 11 | 12 | 13 | 14 |
|---|---|---|---|---|---|
| BENZENE YIELD MOLE % | 57 | 59 | 67 | 54.2 | 55.1 |

EXAMPLE 4

In this example, we prepare a new series of bimetallic catalysts with the same alumina carrier as in example 1. These catalysts are listed below:

| | |
|---|---|
| catalyst 15 : 0.4 % iridium | 0.5 % gallium |
| catalyst 16 : 0.4 % rhodium | 0.5 % manganese |
| catalyst 17 : 0.4 % rhodium | 0.5 % zinc |
| catalyst 18 : 0.4 % iridium | 0.5 % indium |
| catalyst 19 : 0.4 % rhodium | 0.5 % cadmium |

The catalysts are obtained by impregnating the alumina with an aqueous solution containing precursor salts of both metals to be deposited. The iridium and rhodium salts are those descriebd above. The following steps of preparation and the test to which is subjected the obtained catalyst are performed in the manner described in example 3.

The obtained results are summarized in table V below:

TABLE V

| CATALYST | 15 | 16 | 17 | 18 | 19 |
|---|---|---|---|---|---|
| BENZENE YIELD MOLE % | 59 | 61.3 | 67 | 65 | 54 |

EXAMPLE 5

We made use of a catalyst No 20 whose carrier was alumina having the following characteristics:
- specific surface: 29 m²/g
- pore volume: 0.51 cc/g
- percent of n.heptane cracked under the above-mentioned conditions: 1.1% by weight
- neutralization heat (NH$_3$): 4.7 cal/g2 under the above-mentioned conditions.

We prepare a catalyst by dry impregnation of 100 g of alumina with 63 cc of an aqueous solution containing: 16.7 g of an aqueous solution of chloroiridic acid having a 2.4% by weight iridium content, 10 g of a solution of oxaltantalic complex having a 5% by weight tantalum content.

This impregnation is performed at 50° C for 3 hours. After water removal, the solid is dried at 110° C for 4 hours.

The resulting product is then roasted at 500° C in a stream of dry air (20 l per liter of catalyst and per hour) (less than 100 mg of water per m³ of air) for 2 hours.

The final catalyst No 20 has the following composition by weight:
- 0.4% of iridium
- 0.5% of tantalum
- specific surface of 28 m²/g
- pore volume of 48 cc per 100 g
- heat of neutralization by ammonia adsorption of 4.2 calories per gram of catalyst at 320° C and 300 Torr of ammonia pressure.

The catalyst is charged into a tubular reactor, reduced in a hydrogen stream at 550° C for 15 hours and the feed charge to be hydrodealkylated is passed over said catalyst in the operating conditions mentioned in example 1.

The compositions of the feed charge and the products obtained at the outlet of the reactor, after cooling and separation of the hydrogen from the hydrocarbon gases, are summarized in table VI below:

TABLE VI

| COMPOSITION BY MOLE % | CHARGE | EFFLUENT |
|---|---|---|
| n.hexane | 0.5 | — |
| benzene | 4 | 53.8 |
| toluene | 70 | 41 |
| ethyl benzene | 17 | 2.1 |
| xylenes | 8.5 | 2.4 |
| heavy products (aromatics having more than 8 carbon atoms) | — | undetectable |

As in example 1, practically no degradation of the aromatic ring is observed, the total number of aromatic moles recovered corresponding, with the exception of a difference due to experimental errors, to the total number of moles introduced into the reactor. The gaseous hydrocarbons are consequently produced substantially exclusively by dealkylation of alkylaromatic hydrocarbons or by cracking of the paraffins already present in the feed charge. Accordingly, the benzene yield may be easily determined from the data of table VI. In the present case, it amounts to 54.1 moles of benzene per 100 moles of aromatics charged into the reactor.

As in example 1, it must be observed that this yield is maintained at a remarkable stable level over all the test period of 300 hours, that the formation of heavy products is undetectable and that the coke content of the catalyst, after said test, was found nill.

EXAMPLE 5 A (comparative)

In this example, we compare the performances obtained with catalyst No 20 described in example 5, and those achieved with a catalyst No 21 containing 0.4% of iridium and 0% of tantalum.

This catalyst and that of the invention have been tested under the same conditions as in example 1. Of course, the results obtained with catalyst No 21 are the same as those obtained in example 1 A with the catalyst No 2, the catalysts No 2 and No 21 being different only with respect to the alumina structure.

The benzene yields as well as the percent of heavy products formed with respect to the amount of the feed charge, are compared in table VII:

TABLE VII

| REACTION TEMPERATURE °C | CATALYST ACCORDING TO THE INVENTION YIELD MOLE % | | CATALYST OF EXAMPLE 1 A : YIELD MOLE % | |
|---|---|---|---|---|
| | BENZENE | $C_9^+$ | BENZENE | $C_9^+$ |
| 550 | 53.8 | — | 51 | 0 |
| 570 | 69.5 | 0 | 66 | 0 |
| 590 | 83 | 0 | 78 | 0.1 |
| 600 | 85.2 | 0.1 | 78 | 0.1 |

It is apparent that by using the catalyst of the invention, we obtain a benzene yield substantially higher than that obtained with the other catalyst.

The introduction of tantalum gives to the catalyst a better activity and selectivity.

EXAMPLE 5 B (comparative)

It is recalled, by way of comparison, that the charge of example 1 has been hydrodealkylated, in example 1 B, in the presence of a conventional hydrodealkylation catalyst containing 7.5% of chromium oxide deposited on alumina having a specific surface of 170 m²/g, a pore volume of 0.60 cc/g, and a heat of neutralization, by ammonia adsorption, of 18 calories per gram of catalyst, at 320° C, under a reduced pressure of 300 mm of Hg.

When proceeding under the operating conditons of example 1 (550° C, 12 kg/cm², VVH: 4 and relative hydrogen flow rate of 5.7 moles per mole of hydrocarbon of the charge), we have obtained, after 300 hours, a molar benzene yield of 4% and a $C_9^+$ mole content of 0%.

The results were thus very poor.

If we proceed, on the contrary, in the presence of the chromium catalyst of example 1 B, under conventional conditions, at 650° C, at a pressure of 40 kg/cm², with a VVH of 1 and a ratio $H_2/H_C$ of 5, we obtain, after 300 hours, a benzene yield of 58% by mole with a $C_9^+$ mole content of 3.5% these results being acceptable although however subtantially lower than those obtained when operating under milder conditions with a catalyst such as that of example 5.

EXAMPLE 5 C (comparative)

By way of comparison, we make use of catalysts 20 and 21 of examples 5 and 5 A, for hydrodealkylating the feed charge of example 5 under the following conventional operating conditions:
  temperature: 650° C
  pressure: 40 kg/cm²
  VVH: 4
  ratio $H_2/H_C$: 5

After 300 hours of operation, we obtained a molar benzene yield of 85.4% and a molar content of $C_9^+$ of about 1.9% with the catalyst of examples 5 as compared to 75% and 0.3% respectively with the iridium catalyst of example 5 A alone. Proceeding at a too high temperature has the inconvenience of leading to the formation of heavy products which would not be formed when operating under milder conditions.

EXAMPLE 6

In this example, we make use of a series of catalysts having the same alumina carrier as that used in example 5.

The following is the list of the catalysts with their composition by weight:

| Catalysts | | |
|---|---|---|
| No 22 | 0.4 % platinum | 0.5 % tantalum |
| No 23 | 0.4 % platinum | 0.5 % niobium |
| No 24 | 0.4 % platinum | 0.5 % copper |
| No 25 | 0.4 % platinum | 0.5 % silver |
| No 26 | 0.4 % platinum | 0.5 % gold |
| No 27 | 0.4 % platinum | 0.5 % titanium |

These catalysts are obtained by double impregnation of the carrier, according to the technqiue already described in example 5, although said technique is not the only which can be used. For the preparation of these catalysts, we made use of aqueous solutions of the following compounds: chloroplatinic acid, oxaltantalic and oxalniobic complexes, copper and silver nitrates, chloroauric acid and titanium oxichloride.

As a matter of fact these catalysts give as good results when they are prepared in a single impregnation step, i.e. with a solution containing both associated elements as with a double impregnation, by first introducing the plantinum, drying and roasting and then introducing the second element.

These various catalysts are then charged into a tubular reactor, reduced at 550° C for 15 hours in a $H_2$ stream and tested under the conditions of example 5 with the charge described in example 5. The benzene yields obtained after 100 hours of run with these various catalysts are summarized in table VIII.

TABLE VIII

| CATALYST | 22 | 23 | 24 | 25 | 26 | 27 |
|---|---|---|---|---|---|---|
| BENZENE YIELD MOLE % | 53.2 | 53 | 52.1 | 54 | 53.6 | 54.2 |

EXAMPLE 7

In this example we prepare a series of bimetallic catalysts on the alumina carrier of example 5.

The list of these catalysts as well as their composition by weight is given below:

| Catalysts | Composition | |
|---|---|---|
| No 28 | 0.4 % iridium | 0.5 % gold |
| No 29 | 0.4 % ruthenium | 0.5 % silver |
| No 30 | 0.4 % rhodium | 0.5 % copper |

The catalysts are obtained by impregnating the alumina carrier with an aqueous solution containing, on the one hand, the iridium, ruthenium, rhodium, cobalt and palladium salts such as above-described and, on the other hand, the additional selected metal chlorides. The solids obtained after impregnation are then treated in the same manner as the catalysts of example 5, except that the reduction step is conducted at 580° C for 15 hours.

The results obtained after the test, carried out in the same conditions as in example 5, are summarized in table IX below:

TABLE IX

| CATALYST | 28 | 29 | 30 |
|---|---|---|---|
| BENZENE YIELD MOLE % | 53 | 53.1 | 54 |

EXAMPLE 8

In this example, we made use of a series of bimetallic catalysts having the same alumina carrier as used in example 5.

The catalysts which have been prepared and tested are as follows:

| Catalysts | | Composition |
|---|---|---|
| No 31 | 0.4 % iridium | 0.5 % copper |
| No 32 | 0.4 % cobalt | 0.5 % copper |
| No 33 | 0.4 % platinum | 0.5 % titanium |
| No 34 | 0.4 % palladium | 0.5 % yttrium |
| No 35 | 0.4 % cobalt | 0.5 % gold |

The catalysts are obtained by impregnation of alumina with an aqueous solution containing the precursor salts of both metals which have to be deposited. The salts of metals from the group VIII are those above-described. As salts of the other introduced elements we made use of: chloroauric acid, titanium oxichloride, copper and yttrium nitrates. The subsequent steps of the preparation and the test of the resulting catalysts are performed in the same manner as in example 7.

The obtained results are summarized in table X below:

TABLE X

| CATALYST | 31 | 32 | 33 | 34 | 35 |
|---|---|---|---|---|---|
| BENZENE YIELD MOLE % | 54 | 54.3 | 53.2 | 53.1 | 54.5 |

EXAMPLE 9

In this example, we have prepared new bimetallic catalysts which are as follows:

| Catalysts | | |
|---|---|---|
| No 36 | 0.5 % cobalt | 0.5 % cadmium |
| No 37 | 15 % cobalt | 0.5 % cadmium |
| No 38 | 0.5 % cobalt | 0.5 % gallium |
| No 39 | 15 % cobalt | 0.5 % gallium |
| No 40 | 0.5 % cobalt | 0.5 % indium |
| No 41 | 15 % cobalt | 0.5 % indium |
| No 42 | 0.5 % cobalt | 0.5 % thallium |
| No 43 | 15 % cobalt | 0.5 % thallium |
| No 44 | 0.5 % cobalt | 0.5 % zinc |
| No 45 | 15 % cobalt | 0.5 % zinc |
| No 46 | 0.5 % cobalt | 0.5 % manganese |
| No 47 | 15 % cobalt | 0.5 % manganese |
| No 48 | 0.5 % cobalt | 0.5 % copper |
| No 49 | 15 % cobalt | 0.5 % copper |
| No 50 | 0.5 % cobalt | 0.5 % gold |
| No 51 | 15 % cobalt | 0.5 % gold |
| No 52 | 0.5 % cobalt | 0.5 % silver |
| No 53 | 15 % cobalt | 0.5 % silver |
| No 54 | 0.5 % cobalt | 0.5 % titanium |
| No 55 | 15 % cobalt | 0.5 % titanium |
| No 56 | 0.5 % cobalt | 0.5 % niobum |
| No 57 | 15 % cobalt | 0.5 % niobum |
| No 58 | 0.5 % cobalt | 0.5 % tantalum |
| No 59 | 15 % cobalt | 0.5 % tantalum |

Catalysts No 36 to No 47 have been prepared with the same alumina carrier as in example 1 while catalysts 48 to 59 have been prepared with the same alumina carrier as in example 5. All of these catalysts have been prepared by means of an aqueous solution containing, on the one hand, cobalt nitrate and, on the other hand, a salt of the selected additional metal. The resulting products have been treated, after impregnation of the alumina, as described above for the other catalysts of the preceding examples.

Catalysts 36 to 47 are charged into a tubular reactor and reduced in a hydrogen stream at 550° C for 15 hours. The feed charge of example 1 is then passed over these catalysts under the same operating conditions as in example 1. The benzene yields obtained after 100 hours of run over these various catalysts, are reported in table XI.

TABLE XI

| CATALYST No | BENZENE YIELD (mole %) |
|---|---|
| 36 | 54 |
| 37 | 55 |
| 38 | 54 |
| 39 | 57 |
| 40 | 55.5 |
| 41 | 56 |
| 42 | 54.5 |
| 43 | 55.5 |
| 44 | 55 |
| 45 | 56.5 |
| 46 | 55.1 |
| 47 | 56.3 |

The catalysts containing 15% of cobalt appear to give better results than those which contain only 0.5% of cobalt.

When proceeding under the following more severe conditions:
temperature: 590° C
pressure: 20 bars
VVH: 4
ratio $H_2/H_C$: 5 it is observed from table XII that the catalysts having a high cobalt content (15%) have a better stability after 300 hours of run and are also more selective than the catalysts which only contain 0.5 of cobalt.

TABLE XII

| CATALYST | BENZENE YIELD (mole %) | $C_9^+$ (mole %) |
|---|---|---|
| No 36 | 70 | 1.2 |
| 37 | 74 | 0.1 |
| 38 | 71 | 1.3 |
| 39 | 75.5 | 0.15 |
| 40 | 71.5 | 1.2 |
| 41 | 76 | 0.2 |
| 42 | 72 | 1.5 |
| 43 | 76 | 0.2 |
| 44 | 71.5 | 1.1 |
| 45 | 76.5 | 0.1 |
| 46 | 71.8 | 1.2 |

TABLE XII-continued

| CATALYST | BENZENE YIELD (mole %) | $C_9^+$ (mole %) |
|---|---|---|
| 47 | 76.2 | 0.1 |

The catalysts 48 to 59 have been charged into a tubular reactor, reduced in a hydrogen stream, at 550° C, for 15 hours. The charge of example 1 is passed over these various catalysts, but under more severe conditions than in example 1, said conditions being those corresponding to table XII, i.e.:
 temperature: 590° C
 pressure: 20 bars
 VVH: 4
 ratio $H_2/H_C$: 5

It is observed, from the following table XIII, that, after 300 hours of run, the catalysts having a high cobalt content (15%) have a better stability and, after 300 hours, are more selective than the catalysts which contain only 0.5% of cobalt.

TABLE XIII

| CATALYST No | BENZENE YIELD (mole %) | $C_9^+$ (mole %) |
|---|---|---|
| 48 | 69 | 1.8 |
| 49 | 74.5 | 0.1 |
| 50 | 68 | 1.60 |
| 51 | 74 | 0.15 |
| 52 | 67.5 | 1.7 |
| 53 | 74 | 0.15 |
| 54 | 70 | 1.30 |
| 55 | 75 | 0.20 |
| 56 | 70.5 | 1.30 |
| 57 | 75.5 | 0.17 |
| 58 | 70 | 1.5 |
| 59 | 75.5 | 0.2 |

EXAMPLE 10

We made use of a catalyst No. 60 whose carrier is an alumina having the following characteristics:
 specific surface: 25 m²/g
 pore volume: 0.55 cc/g
 percent of n.heptane cracked under the above-described conditions: 1.00% by weight
 neutralization heat (NH₃) as determined under the above-described conditions: 4.5 cal/g.

The catalyst of said example has been prepared by dry impregnation of 100 g of said alumina with 60 cc of an aqueous solution containing:
 0.6 g of rhenium in the form of perrhenic acid,
 8 g of molybdenum in the form of ammonium molybdate.

The contact is maintained at 50° C for 3 hours. After decantation, the product is dried at 110° C for 4 hours. The resulting product is then roasted at 500° C in a stream of dry air (20 liters per liter of catalyst and per hour), containing less than 100 mg of water per cubic meter of air.

The final catalyst No. 60. contains by weight:
 0.6% of rhenium
 8% of molybdenum and it has the following characteristics:
 specific surface: 23 m²/g
 pore volume: 53 cc/100 g
 neutralization heat (NH₃ adsorption): 4.8 calories/g at 320° C under an ammonia pressure of 300 Torr.

Said catalyst is charged into a tubular reactor and reduced in a hydrogen stream at 560° C for 15 hours. The charge is passed over this reduced catalyst under the following operating conditions which are the same as in example 1:
 total pressure: 12 bars
 temperature: 550° C
 VVH: 4 volumes of liquid charge per volume of catalyst and per hour
 hydrogen relative flow rate: 5.7 moles per mole of hydrocarbon of the feed charge.

In table XIV below, are summarized the compositions of the feed charge and of the reactor effluent after cooling and removal of hydrogen and light hydrocarbons (lower than C6).

TABLE XIV

| Composition by mole % | Feed charge | Effluent |
|---|---|---|
| n.hexane | 0.5 | — |
| benzene | 4 | 54 |
| toluene | 70 | 40 |
| ethyl benzene | 17 | 2.4 |
| xylenes | 8.5 | 2.5 |
| heavy products (aromatics having more than 8 carbon atoms) | — | undetectable |

It is observed, as in example 1, that practically no degradation of the aromatic ring occurs, the total number of aromatic moles recovered corresponding, with the difference due to experimental errors, to the total number of moles introduced into the reactor. The gaseous hydrocarbons are accordingly, substantially exclusively produced by dealkylation of alkyl aromatic hydrocarbons or by cracking of the paraffins present in the charge. The benzene yield obtained is, accordingly, very easy to determine from the data of table XIV. In the present case, it amounts to 54.3 moles of benzene produced per 100 moles of aromatics charged into the reactor.

It is also noticeable that this yield is maintained with a remarkable stability over all the test period which was 300 hours.

It should be noted that the formation of heavy products is undetectable and that the coke content of the catalyst, after this test, was found nill.

EXAMPLE 10 A (comparative)

In this example, the performances obtained with the catalyst No. 60. described in example 10 are compared with those of the two catalysts 61 and 62, respectively containing 0.6% of rhenium and 8% of molybdenum.

These catalysts and the catalyst of the invention have been tested under the same conditions as described in example 10.

The benzene yields as well as the amount of the formed heavy products, in percentage of the total charge introduced, are compared in the following table XV.

TABLE XV

| Reaction temperature °C | Yields in % by mole when using different catalysts | | | | | |
|---|---|---|---|---|---|---|
| | Catalyst 60 0.6 % Re 8% Mo | | Catalyst 61 0.6% Re 0% Mo | | Catalyst 62 0 % Re 8% Mo | |
| | Benzene | $C_9^+$ | Benzene | $C_9^+$ | Benzene | $C_9^+$ |
| 550 | 54 | — | 48 | 0 | 50 | 0 |
| 570 | 69.1 | — | 65 | 0 | 66.4 | 0.1 |
| 590 | 82.2 | 0 | 75 | 0.2 | 77 | 0.2 |
| 600 | 85.1 | 0.15 | 75 | 0.25 | 75 | 0.4 |

It is apparent that the catalyst of the invention provides a benzene yield substantially higher and a far better selectivity (formation of a lower amount of heavy products) than those obtained with rhenium catalyst or molybdenum catalyst along.

The association of both metals substantially increases the performances of catalyst 60 according to the invention.

Example 10 B (comparative)

By way of comparison, it must be stated again that the feed charge of example 1 has been hydrodealkylated according to example 1 B, in the presence of a conventional hydrodealkylation catalyst containing 7.5% of chromium oxide deposited on an alumina having a specific surface of 170 m²/g, a pore volume of 0.60 cc/g and a heat of neutralization by ammonia adsorption of 18 calories per gram of catalyst at 320° C under the reduced pressure of 300 mm Hg.

By proceeding under the same operating conditions as in example 1 (550° C, 12 kg/cm², VVH: 4 and a relative hydrogen flow rate of 5.7 moles per mole of hydrocarbon of the feed charge), we obtain, after 300 hours, a molar benzene yield of 4% and a molar $C_9^+$ content of 0%.

The results are, clearly, very poor.

On the contrary, when operating in the presence of the chromium-containing catalyst of example 1 B, in a conventional manner, at 650° C, under a pressure of 40 kg/cm², with a VVH of 1 and a ratio $H_2/H_C$ of 5, we have obtained, after 300 hours, a molar benzene yield of 58% and a molar content of $C_9^+_0$ amounting to 3.5%, these results being acceptable although they are not so good as when operating with a catalyst such as described in example 10 and under milder conditions.

EXAMPLE 10 C (comparative)

By way of comparison, we make use of catalysts 60, 61 and 62 of examples 10 and 10 A for hydrodealkylating the feed charge of example 10 under the following conventional operating conditions:
temperature: 650° C
pressure: 40 kg/cm²
VVH: 4
ratio $H_2/H_C$: 5

After 300 hours, we obtain a benzene yield of 83.8% (by mole) and a $C_9^+$ molar content of about 1.8% with catalyst 60 of example 10 as compared with 71.7% and 2.5% respectively for catalyst 61, containing only rhenium and 72.6% and 2.4% respectively for catalyst 62 containing only molybdenum.

To proceed at too high a temperature has the inconvenience of leading to the formation of heavy products, which can be avoided by operating under milder conditions.

EXAMPLE 11

In this example, we use a series of catalysts having the same alumina carrier as that used in example 10.

A list of these catalysts is given below with their composition by weight.

| Catalysts | | | | |
|---|---|---|---|---|
| No 63 | rhenium | 0.6 % | molybdenum | 8 % |
| No 64 | molybdenum | 5 % | tungsten | 5 % |
| No 65 | rhenium | 0.6 % | chromium | 8 % |
| No 66 | tungsten | 8 % | copper | 1 % |
| No 67 | tungsten | 8 % | silver | 1 % |
| No 68 | tungsten | 8 % | gold | 1 % |
| No 69 | rhenium | 0.6 % | gold | 0.5 % |
| No 70 | molybdenum | 8 % | silver | 1 % |
| No 71 | chromium | 5 % | tungsten | 5 % |
| No 72 | rhenium | 0.6 % | manganese | 3 % |
| No 73 | molybdenum | 5 % | copper | 1 % |
| No 74 | molybdenum | 5 % | gold | 1 % |
| No 75 | rhenium | 0.6 % | copper | 0.7 % |
| No 76 | rhenium | 0.6 % | silver | 1 % |
| No 77 | chromium | 5 % | molybdenum | 6 % |
| No 78 | rhenium | 0.6 % | tungsten | 5 % |
| No 79 | tungsten | 8 % | manganese | 2 % |
| No 80 | chromium | 5 % | manganese | 2 % |
| No 81 | molybdenum | 8 % | manganese | 2 % |

These catalysts have been obtained by a double impregnation of the carrier according to the technique described above in example 10, although this technique is not only one which can be used.

As a matter of fact, these catalysts give as good results when they are prepared with a single impregnation, i.e. with a solution containing both associated elements as when they are prepared with a double impregnation i.e. by introduction of a first constituent in a first step followed with drying and roasting and introduction of a second element. In order to prepare said catalysts, we made use of aqueous solutions containing the elements to be deposited on the carrier. Said elements are in the form of complex salts or the corresponding organometallic derivatives, soluble in water or in suitable solvents. We will use, for example, rhenium heptoxide, ammonium perrhenate, molybdates, tungstates, chromic anhydride, ammonium chromate, chlorides, nitrates and other soluble salts of rhenium, tungsten, chromium, copper, silver, molybdenum, gold and manganese.

These various catalysts are then charged into a tubular reactor, reduced at 550° C for 15 hours in a $H_2$ stream and tested in the conditions of example 10 with the charge described in example 10. The benzene yield obtained after 100 hours of run with these various catalysts are summarized in table XVI.

TABLE XVI

| Catalyst | Benzene yield (mole %) |
| --- | --- |
| 63 | 53.4 |
| 64 | 53.1 |
| 65 | 52.5 |
| 66 | 53.5 |
| 67 | 53.6 |
| 68 | 53.5 |
| 69 | 52 |
| 70 | 52.8 |
| 71 | 52.5 |
| 72 | 53.1 |
| 73 | 52.8 |
| 74 | 53.4 |
| 75 | 53.4 |
| 76 | 52.9 |
| 77 | 52.9 |
| 78 | 53 |
| 79 | 53.2 |
| 80 | 53 |
| 81 | 53.3 |

EXAMPLE 12

In this example, we have prepared a series of bimetallic catalysts with the alumina carrier of example 10.

The list of these catalysts as well as their composition by weight is given below:

| Catalysts | Compositions | | | |
| --- | --- | --- | --- | --- |
| 82 | tungsten | 8 % | zinc | 1 % |
| 83 | molybdenum | 8 % | cadmium | 1 % |
| 84 | chromium | 8 % | gallium | 1 % |
| 85 | molybdenum | 8 % | indium | 1 % |
| 86 | tungsten | 8 % | thallium | 1 % |
| 87 | rhenium | 1 % | germanium | 0.5 % |
| 88 | chromium | 8 % | tin | 1 % |
| 89 | molybdenum | 8 % | lead | 1 % |
| 90 | rhenium | 4 % | zinc | 1 % |
| 91 | rhenium | 4 % | cadmium | 1 % |
| 92 | rhenium | 4 % | gallium | 1 % |
| 93 | rhenium | 4 % | indium | 1 % |
| 94 | rhenium | 4 % | thallium | 1 % |
| 95 | rhenium | 2 % | tin | 1 % |
| 96 | rhenium | 2 % | lead | 1 % |
| 97 | chromium | 8 % | copper | 0.5 % |
| 98 | molybdenum | 8 % | gallium | 1 % |
| 99 | molybdenum | 8 % | tin | 1 % |
| 100 | tungsten | 8 % | gallium | 1 % |
| 101 | tungsten | 8 % | indium | 1 % |
| 102 | tungsten | 8 % | germanium | 1 % |
| 103 | tungsten | 8 % | tin | 1 % |
| 104 | tungsten | 8 % | lead | 1 % |
| 105 | manganese | 4 % | copper | 1 % |
| 106 | manganese | 4 % | gold | 1 % |
| 107 | manganese | 4 % | silver | 1 % |
| 108 | manganese | 4 % | zinc | 1 % |
| 109 | manganese | 4 % | lead | 1 % |
| 110 | manganese | 4 % | tin | 1 % |

These catalysts are obtained by impregnation of an alumina carrier by means of aqueous solutions containing, on the one hand, tungsten, molybdenum, chromium, rhenium and manganese derivatives such as above-described and, on the other hand, zinc, cadmium, gallium, indium, thallium, germanium, tin, lead, copper, gold and silver chlorides. The solids obtained after impregnation are then treated in the same manner as the catalysts of example 1.

All these catalysts, tested under the same conditions as in example 10, have provided benzene yields (in mole %) as reported in table XVII below:

TABLE XVII

| Catalyst | Benzene yield (mole %) |
| --- | --- |
| 82 | 53.1 |
| 83 | 52.1 |
| 84 | 52 |
| 85 | 53.9 |
| 86 | 54 |
| 87 | 52.5 |
| 88 | 52.5 |
| 89 | 52 |
| 90 | 52.7 |
| 91 | 53 |
| 92 | 52.9 |
| 93 | 52.4 |
| 94 | 52.2 |
| 95 | 53.5 |
| 96 | 53.1 |
| 97 | 53.4 |
| 98 | 52.2 |
| 99 | 53.4 |
| 100 | 53.6 |
| 101 | 53.1 |
| 102 | 52.2 |
| 103 | 52.4 |
| 104 | 52.8 |
| 105 | 52.8 |
| 106 | 53.5 |
| 107 | 53.5 |
| 108 | 53.1 |
| 109 | 53.7 |
| 110 | 53.6 |

We claim:

1. A process for the catalytic hydrodealkylation of alkylaromatic hydrocarbons, conducted at a temperature from 400° to 650° C in the presence of hydrogen, under a pressure from 1 to 40 kg/cm$^2$, with a spatial velocity from 1 to 10 and a ratio of the hydrogen to the hydrocarbon, expressed in moles by mole at the outlet of the reactor from 1 to 10, and in the presence of a catalyst selected from one of the catalysts A and B, in which:

catalyst A essentially contains:
  a. a carrier,
  b. at least one metal selected from a first group consisting of cobalt, ruthenium, osmium, palladium, rhodium, iridium and platinum, at a metal concentration from 0.05 to 20% by weight of catalyst when the selected metal is cobalt and from 0.05 to 5% by weight of the catalyst when the selected metal is chosen from the group consisting of ruthenium, osmium, palladium, rhodium, iridium and platinum,
  c. at least one additional metal selected from a second group consisting of zinc, cadmium, gallium, indium, thallium, manganese, silver, gold, yttrium, titanium, niobium and tantalum, said metal being at a concentration from 0.05 to 5% by weight of the catalyst;

catalyst B contains essentially:
  a. a carrier,
  b. at least one metal selected from a first group consisting of chromium, molybdenum, tungsten, rhenium and manganese, the metal concentration being from 0.05 to 20% by weight of the catalyst.
  c. at least one additional metal, said additional metal being chosen different from the selected metal of the first group, this additional metal being selected from the group consisting of chromium, molybdenum, tungsten, rhenium, manganese, copper, gold, zinc, cadmiun, gallium, indium, thallium, germanium, the metal concentration being from 0.05 to 20% by weight of the catalyst.

2. A process according to claim 1, conducted at a temperature from 500° to 620° C, under a pressure from 1 to 30 kg/cm², at a spatial velocity from 2 to 8 and a ratio of hydrogen to hydrocarbon, expressed in moles per mole at the outlet of the reactor, from 3 to 8.

3. A process according to claim 2, wherein the pressure is from 1 to 20 kg/cm².

4. A process according to claim 3, wherein the carrier for catalyst A or catalyst B is alumina.

5. A process according to claim 4, wherein the specific surface of catalyst A or B, is from 1 to 100 m²/g.

6. A process according to claim 5, wherein catalyst A contains 1 to 17% by weight of metal from the first group when the selected metal is cobalt or from 0.1 to 1% when of ruthenium, osminum, palladium, rhodium, iridium or platinum and in which the concentration of additional metal selected from the second group is from 0.1 to 2% by weight of the catalyst.

7. A process according to claim 5, wherein catalyst B contains 0.1 to 10% with respect to the catalyst weight, of metal from the first group and 0.1 to 5% with respect to the catalyst weight, of said additional metal.

8. A process according to claim 6, wherein the total pore volume of catalyst A is from 0.2 to 0.8 cc/g and the heat of neutralization of the catalyst by ammonia adsorption is lower than 10 calories per gram of catalyst at 320° C under a pressure of 300 mm Hg.

9. A process according to claim 8, wherein the specific surface of catalyst A is from 5 to 80 m²/g.

10. A process according to claim 7, wherein the total pore volume of catalyst B is from 0.2 to 0.8 cc/g and the heat of neutralization of the catalyst by ammonia adsorption is lower than 10 calories per gram of catalyst at 320° C under a reduced pressure of 300 mm of mercury.

11. A process according to claim 10, wherein the specific surface of catalyst B is from 5 to 80 m²/g.

12. A process according to claim 1 wherein said catalyst contains rhodium and gallium.

13. A process according to claim 1 wherein said catalyst contains rhodium and manganese.

14. A process according to claim 1 wherein said catalyst contains rhodium and zinc.

15. A process according to claim 1 wherein said catalyst contains iridium and indium.

16. A process according to claim 1 wherein said catalyst contains iridium and gallium.

17. A process according to claim 1 wherein said catalyst contains iridium and zinc.

18. A process according to claim 1 wherein said catalyst contains ruthenium and manganese.

19. A process according to claim 1 wherein said catalyst contains cobalt and a metal selected from gallium, indium, zinc and manganese.

20. A process according to claim 19 wherein catalyst contains cobalt and gallium.

21. A process according to claim 19 wherein said catalyst contains cobalt and indium.

22. A process according to claim 19 wherein said catalyst contains cobalt and zinc.

23. A process according to claim 19 wherein said catalyst contains cobalt and manganese.

24. A process according to claim 1, wherein said catalyst contains iridium-zinc, ruthenium-manganese, rhodium-gallium, iridium-gallium, rhodium-manganese, rhodium-zinc, iridium-indium, cobalt-gallium, cobalt-indium, cobalt-zinc or cobalt-manganese.

25. A process according to claim 24, wherein the carrier is alumina.

26. A process according to claim 25, wherein said catalyst contains cobalt-gallium, cobalt-indium, cobalt-zinc or cobalt-manganese and the amount of cobalt is from 1 to 17% by weight.

* * * * *